US011760803B2

(12) United States Patent
Brake et al.

(10) Patent No.: US 11,760,803 B2
(45) Date of Patent: Sep. 19, 2023

(54) METHODS OF TREATING GASTROINTESTINAL IMMUNE-RELATED ADVERSE EVENTS IN IMMUNE ONCOLOGY TREATMENTS

(71) Applicant: Millennium Pharmaceuticals, Inc., Cambridge, MA (US)

(72) Inventors: Rachael L. Brake, Natick, MA (US); Eric H. Westin, Concord, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/087,246

(22) PCT Filed: Mar. 24, 2017

(86) PCT No.: PCT/US2017/024033
§ 371 (c)(1),
(2) Date: Sep. 21, 2018

(87) PCT Pub. No.: WO2017/165778
PCT Pub. Date: Sep. 28, 2017

(65) Prior Publication Data
US 2019/0040140 A1 Feb. 7, 2019

Related U.S. Application Data

(60) Provisional application No. 62/312,671, filed on Mar. 24, 2016.

(51) Int. Cl.
| | | |
|---|---|---|
| *A61K 39/395* | (2006.01) | |
| *A61K 39/00* | (2006.01) | |
| *C07K 16/28* | (2006.01) | |
| *A61P 37/06* | (2006.01) | |
| *A61P 35/00* | (2006.01) | |

(52) U.S. Cl.
CPC .......... *C07K 16/2845* (2013.01); *A61P 35/00* (2018.01); *A61P 37/06* (2018.01); *C07K 16/2803* (2013.01); *C07K 16/2818* (2013.01); *C07K 16/2839* (2013.01); *C07K 16/2878* (2013.01); *A61K 2039/507* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,147,851 B1 | 12/2006 | Ponath et al. |
| 7,402,410 B2 | 7/2008 | Ponath et al. |
| 9,663,579 B2 | 5/2017 | Fox et al. |
| 9,764,033 B2 | 9/2017 | Diluzio et al. |
| 10,004,808 B2 | 6/2018 | Fox et al. |
| 10,040,855 B2 | 8/2018 | Diluzio et al. |
| 10,143,752 B2 | 12/2018 | Fox et al. |
| 2012/0282249 A1* | 11/2012 | Fox .................. A61K 39/39591 424/133.1 |

FOREIGN PATENT DOCUMENTS

| | | |
|---|---|---|
| EP | 3012270 A1 | 4/2016 |
| WO | 1996/24673 A1 | 8/1996 |
| WO | 1998/06248 A3 | 5/1998 |
| WO | 01/078779 A3 | 7/2002 |
| WO | 2007/061679 A1 | 5/2007 |
| WO | 2012/151247 A3 | 2/2013 |
| WO | 2012/151248 A3 | 2/2013 |
| WO | 2016/086147 A1 | 6/2016 |
| WO | 2016/105572 A1 | 6/2016 |

OTHER PUBLICATIONS

Fecher et al. Ipilimumab and Its Toxicities: A Multidisciplinary Approach. The Oncologist 2013;18:733-743 (Year: 2013).*
Weber et al. Management of Immune-Related Adverse Events and Kinetics of Response With Ipilimumab. J Clin Oncol 30:2691-2697. (Year: 2012).*
Asim Amin. Managing Side Effects of Immunotherapy: Diarrhea/Colitis. Medscape Carolinas Healthcare System, Levien Cancer Institute, Dec. 23, 2015, pp. 1-3, (Year: 2015).*
Postow et al. Nivolumab and Ipilimumab versus Ipilimumab in Untreated Melanoma. N Engl J Med 372;May 21, 2015. (Year: 2015).*
Postow, Managing Side Effects of Immune Checkpoint Blockade. Fourteenth International Kidney Cancer Symposium, Nov. 6-7, 2015. pp. 1-38. (Year: 2015).*
FDA Updates, Opdivo-Yervoy Combination Approved for Melanoma First Combination-Immunotherapy Regimen for Cancer. Nov. 10, 2015—vol. 37—Issue 21—p. 39. (Year: 2015).*
Larkin et al. Combined Nivolumab and Ipilimumab or Monotherapy in Untreated Melanoma. N Engl J Med 373;1, Jul. 2, 2015. (Year : 2015).*
Somasundaram and Herlyn. Nivolumab in combination with ipilimumab for the treatment of melanoma. Expert Rev Anticancer Ther. Oct. 2015 ; 15(10): 1135-1141). (Year: 2015).*
Sznol et al. Combined nivolumab (anti-PD-1, BMS-936558, ONO-4538) and ipilimumab in the treatment of advanced melanoma patients: Safety and clinical activity. [Abstract 3734]. European Society for Medical Onocology 2013 Annual Meeting; Sep. 27-Oct. 1, 2013; Amsterdam, Netherlands). (Year: 2013).*

(Continued)

*Primary Examiner* — Maher M Haddad
(74) *Attorney, Agent, or Firm* — Womble Bond Dickinson (US) LLP

(57) ABSTRACT

The invention provides, inter alia, methods of reducing gastrointestinal immune related adverse events, such as colitis and diarrhea, in subjects undergoing an immune treatment, such as an immune oncology treatment, such as anti-CTLA4 antibody and anti-PD-1 antibody combination treatment for melanoma. In certain aspects, the methods encompass administering a therapeutically effective amount of a polypeptide that inhibits MAdCAM-integrin binding, such as an anti-α4β7 integrin antibody, such vedolizumab or a related antibody.

12 Claims, 2 Drawing Sheets

Specification includes a Sequence Listing.

(56) References Cited

OTHER PUBLICATIONS

Wochok et al. Nivolumab plus Ipilimumab in Advanced Melanoma. N Engl J Med 369;2, 2013. (Year: 2013).*
Villadolid and Amin. Immune checkpoint inhibitors in clinical practice: update on management of immune-related toxicities. Transl Lung Cancer Res. 4(5):560-575, Oct. 2015 (Year: 2015).*
Harris and Faleck. Effectiveness of Vedolizumab in Patients With Refractory Immunotherapy-Related Colitis: a Case Series. Abstract 086, Gastroenterology, 158(3) supplement, p. S119. Feb. 2020. (Year: 2020).*
Hirten et al. Vedolizumab and Infliximab Combination Therapy in the Treatment of Crohn's Disease. Am J Gastroenterol. Dec. 2015; 110(12):1737-8. (Year: 2015).*
Supplement to: Postow MA, Chesney J, Pavlick AC, et al. Nivolumab and ipilimumab versus ipilimumab in untreated melanoma. N Engl J Med 2015;372:2006-17. (Year: 2015).*
FDA. Yervoy (ipilimumab) injection, for intravenous use Initial U.S. Approval: 2011. p. 1-62. (Year: 2011).*
Lavinia et al., "Management of toxicities of immune checkpoint inhibitors," Cancer Treatment Reviews, vol. 44:51-60 (2016).
Raine, "Vedolizumab for inflammatory bowel disease: Changing the game, or more of the same?" United European Gastroenterology Journal, vol. 2(5):333-344 (2014).
Anonymous, "Study to Evaluate the Safety, Tolerability, and Pharmacodynamics of Investigational Treatments in Combination with Standard of Care Immune Checkpoint Inhibitors in Participants with Advanced Melanoma," (Jun. 25, 2016) Retrieved from the Internet: https://clinicaltrials.gov/ct2/show/record/NCT02723006 on Jun. 6, 2017.
Hsieh et al., "Vedolizumab: a novel treatment for ipilimumab-induced colitis," BMJ Case Reports (2016).
Navarini et al., "Vedolizumab as a successful treatment of CTLA-4-associated autoimmune enterocolitis," Journal of Allergy and Clinical Immunology, vol. 139(3):1043-1046 (2016).
Viktoria et al., "Vedolizumab treatment for immune checkpoint inhibitor-induced enterocolitis," Cancer Immunology, Immunotherapy, Springer, Berlin/Heidelberg, vol. 66(5):581-592 (2017).
International Search Report from PCT/US2017/024033 dated Jun. 16, 2017.
Cheng et al., "Ipilimumab-induced toxicities and the gastroenterologist," Journal of Gastroenterology and Hepatology 30:657-666 (2015).
Brown, J., et al., "Critical Evaluation of ECV304 as a Human Endothelial Cell Model Defined by Genetic Analysis and Functional Responses: A Comparison with the Human Bladder Cancer Derived Epithelial Cell Line T24/83," Laboratory Investigation,80:37-45 (2000).
Federlin, "Immunological aspects of inflammatory bowel diseases," Immun. Infekt., 6:15-27 (1978) (abstract only).
Fedyk ER, Yang L, Csizmadia V, Yang H, Wyant T. Kadambi VJ, et al. Regional immunomodulation of the gastrointestional tract without systemic immunosuppresion in Cynomolgus macaques by vedolizumab. P-0144 poster (2009).
Fedyk et al.,"The Gastrointestinal-Selective Biologic Vedolizumab Does Not Impair Immune Surveillance of the Central Nervous System in Non-Human Primates," J Crohn's Colitis, 5(1):S13-S14. Abstract P002 (2011).
Fedyk et al., "The Gastrointestinal-Selective Biologic Vedolizumab Does Not Impair Immune Surveillance of the Central Nervous System in Non-Human Primates," Presentation (2011).
Fedyk et al., "The Gastrointestinal-Selective Biologic Vedolizumab Does Not Impair Immune Surveillance of the Central Nervous System in Non-Human Primates." Inflamm Bowel Disease, 17(suppl S1):S4-S5. Abstract O-015 (2011).
Goldenberg, D.M., "New Developments in Monoclonal Antibodies for Cancer Detection and Therapy," CA Cancer J. Clin., 44:43-64 (1994).
Herlyn et al., "Anti-Idiotypic Antibodies Bear the Internal Image of a Human Tumor Antigen," Science 232:100-102 (1986).
Janeway et al., "Immunobiology: The Immune System in Health and Disease", 5th edition. New York: Gartland Science; 2001, p. 95.).
Osband et al., "Problem in the Investigational Study and Clinical use of Cancer Immunotherapy," Immunol. Today, 11:103-105 (1990).
Ribas, A. et al., "Phase III Randomized Clinical Trial Comparing Tremelimumab with Standard-of-Care Chemotherapy in Patients with Advanced Melanoma," J. Clinical Oncology, 31(5): 616-622.
Shaw et al., "Mouse/Human Chimeric Antibodies to a Tumor-Associated Antigen: Biologic Activity of the Four Human IgG Subclasses," J. Natl. Cancer Inst., 80:1553-1559 (1988).
Shiner, "Immunopathology of the Digestive Apparatus in Infancy," Pediatr. Med. Chir. 4:359-364 (1982) (abstract only).
Tang, D.G., et al., "Phenotypic Properties of Cultured Tumor Cells: Integrin .alpha.11.beta.3 Expression, Tumor-Cell-Induced Platelet Aggregation, and Tumor-Cell Adhesion to Endothelium as Important Parameters of Experimental Metastasis," Int. J.Cancer, 54:338-347 (1993).
Beck et al., "Enterocolitis in patients with cancer after antibody blockade of cytotoxic T-lymphocyte-associated antigen 4." J Clin Oncol, May 20, 2006, 24, p. 2283-2289.
Michot et al., "Immune-related adverse events with immune checkpoint blockade: a comprehensive review", European Journal of Cancer, Jan. 5, 2016, 54, p. 139-148.
Randhawa et al., "Vedolizumab in combined immune checkpoint therapy-induced infliximab-refractory colitis in a patient with metastatic melanoma: A case report", J Clin Oncol, Oct. 24, 2019, 10(10), p. 350-357.
"Study to Evaluate the Safety, Tolerability, and Pharmacodynamics of Investigational Treatments in Combination With Standard of Care Immune Checkpoint Inhibitors in Participants With Advanced Melanoma", study version v17 of clinical trial NCT02723006, Apr. 1, 2021.
Haanen et al., "Management of toxicities from immunotherapy: ESMO Clinical Practice Guidelines for diagnosis, treatment and follow-up", Annals of Oncology, Aug. 2017, 28(4), p. iv119-iv142.
Abu-Sbeih et al., J Immunother Cancer. Apr. 2, 2019,7(1):93.
Wolchok et al. Supplementary Protocol, N Engl J Med. Jul. 11, 2013;369(2):122-33
Postow et al. Supplementary Appendix, N Engl J Med. May 21, 2015;372(21):2006-17.

* cited by examiner

METHODS OF TREATING GASTROINTESTINAL IMMUNE-RELATED ADVERSE EVENTS IN IMMUNE ONCOLOGY TREATMENTS

RELATED APPLICATIONS

This application is the U.S. National Stage of International Application No. PCT/US2017/024033 filed Mar. 24, 2017, which claims the benefit of U.S. Provisional Application No. 62/312,671 filed on Mar. 24, 2016. The entire contents of the foregoing applications are hereby incorporated by reference.

FIELD OF THE INVENTION

The present invention relates to methods of ameliorating gastrointestinal immune-related adverse events (gi-irAEs) in subjects undergoing an immune oncology treatment. Exemplary gi-irAEs include colitis and diarrhea and immune oncology treatment can include single agent or combination treatments, such as anti-CTLA4 and/or anti-PD-1 antibodies.

BACKGROUND OF THE INVENTION

Immune oncology is a growing and promising field in the fight against cancer. By turning a subject's immune system against a cancer, in part, by counteracting the immune-suppressive tumor microenvironment, immune oncology provides efficacious treatments without many of the negative side effects of systemic chemotherapy or radiotherapy. Despite this, immune oncology can produce significant gi-irAEs, including colitis and diarrhea. For example, 40%, or more, of subjects undergoing immune oncology treatment with anti-CTLA4 and anti-PD-1 antibodies may experience treatment interruption or treatment discontinuation, thus abrogating much of the benefit of the immune oncology treatment. Accordingly, a need exists for methods of reducing gi-irAEs, such as colitis and diarrhea, in subjects undergoing an immune treatment, such as an immune oncology treatment.

SUMMARY OF THE INVENTION

The invention provides, inter alia, methods of reducing gi-irAEs, such as colitis and diarrhea, in subjects undergoing an immune treatment, such as an immune oncology treatment. The invention is based, at least in part, on Applicant's discovery that a polypeptide that inhibits MAdCAM-α4β7 integrin binding, such as an anti-α4β7 integrin antibody, can advantageously reduce gi-irAEs in a subject undergoing an immune oncology treatment. In contrast to other modalities for reducing gi-irAEs that have systemic effects, such as corticosteroids or anti-Tumor Necrosis Factor (TNF) agents (such as infliximab, adalimumab or etanercept), polypeptides that inhibit MAdCAM-α4β7 integrin binding can reduce gi-irAEs with no significant reduction in efficacy of the immune therapy and with a better safety profile.

As discussed further below, gi-irAEs are acute conditions that stand in contrast to spontaneous and/or chronic autoimmune disease such as inflammatory bowel disease (IBD), and are not known to be mediated by common mechanisms of action. Accordingly, it would not necessarily be expected that a treatment for a spontaneous autoimmune IBD would work for a gi-irAE. There is no animal model information for colitis induced by immune treatments, such as by anti-CTLA4 and/or anti-PD1 treatments. The effectiveness of corticosteroids or infliximab in the management of gi-irAEs has not been confirmed in randomized clinical trials. Although infliximab is registered as a treatment for IBD it also has a broader therapeutic spectrum that includes rheumatoid arthritis, psoriatic arthritis, plaque psoriasis, and ankylosing spondylitis.

Accordingly, in one aspect, the invention provides methods of treating a gastrointestinal immune-related adverse event (gi-irAE) in a mammalian subject undergoing an immune oncology treatment. These methods include the step of administering a therapeutically effective amount of a polypeptide that inhibits MAdCAM-α4β7 integrin binding to the subject. In certain embodiments, the methods can include the step of administering the immune oncology treatment. Naturally, corresponding medical uses, including second medical uses (e.g., as medicaments) and targeted uses of a polypeptide that inhibits MAdCAM-α4β7 integrin binding corresponding to the methods provided by the invention are encompassed as well. Collectively, these methods, medicaments, and uses may be referred to as "methods provided by the invention."

In some embodiments, the immune oncology treatment comprises treatment with a modulator of one or more targets selected from: 4-1BB, B7H3, B7H4, CCR2, CD27, CD40, CD40L, CD244, CSF1R, CTLA4, CXCR4, GITR, IDO, ICOS, KIRs (e.g., KIR2DL1 or KIR2DL3), NKG2A, NKG2D, OX40, RAF kinase, PD-1, PDL-1, PDL-2, TIM-3, VISTA, or combinations thereof. In more particular embodiments, the treatment comprises a modulator of a target that is a T-cell co-receptor, more particularly, an inhibiting receptor, and still more particularly wherein the inhibiting receptor is CTLA4, PD-1, or CTLA4 and PD-1. In certain embodiments, the immune oncology treatment does not comprise modulating CCR2, CTLA4, RAF kinase, or PD-1 (alone or, e.g., together with one or more of CTLA4, CCR2, and RAF kinase).

In certain embodiments, the polypeptide that inhibits MAdCAM-α4β7 integrin binding is an anti-α4β7 integrin antibody, such as an anti-α4β7 integrin antibody that competes with vedolizumab for binding α4β7 integrin, more particularly, where the antibody has the epitopic specificity of vedolizumab, more particularly where the antibody comprises the complementarity determining regions (CDRs) of vedolizumab, still more particularly where the antibody is vedolizumab. In more particular embodiments, the anti-α4β7 integrin antibody is administered at a dose of between about: 1.25 to 8.0 mg/kg. In certain particular embodiments, the anti-α4β7 integrin antibody is administered at a dose of between about: 1.25 to 4.25 mg/kg, 1.75 to 3.75 mg/kg, 2.25 to 3.25 mg/kg, e.g., about 2.86 mg/kg, e.g., about 2.8 mg/kg or about 2.9 mg/kg. In other particular embodiments the anti-α4β7 integrin antibody is administered at a dose of between about: 5.0 to 8.0 mg/kg, 5.5 to 7.5 mg/kg, 6.0 to 7.0 mg/kg, e.g., about 6.43 mg/kg, e.g., about 6.4 mg/kg or about 6.5 mg/kg. In certain embodiments, the anti-α4β7 integrin antibody is administered at a unit dose of about: 108, 150, 165, 200, 216, 250, 300, 350, 400, 450, 500, 550, 600, 650, 700, 750 mg, or more, to a human subject. The anti-α4β7 integrin antibody can be administered at any of the foregoing doses on a variety of schedules, such as once every 1, 2, 3, 4, 5, 6, 7, 8, 9, 10, 11, or 12 weeks, or more, for, e.g., 1, 2, 3, 4, 5, 6, 7, 8, 9, 10, or more administrations, e.g., including use without a predetermined end point. In certain embodiments with multiple administrations, the administrations may be at the same doses, or different doses, e.g., escalated, for example, with a first dose unit dose of 200 mg, with subsequent doses of 450 mg. In some embodiments, the anti-α4β7 integrin antibody is administered to achieve a serum concentration (e.g., a serum trough concentration) of about: 10 μg/ml, or more, e.g., about: 11, 12, 13, 14, 15, 16, 17, 18, 19, 20, 25, 30, 35, 40, 45, 50, 60, 70, 80, 90, 93, or 100 μg/ml, e.g., for a period of at least 20 weeks. In particular embodiments, the anti-α4β7 integrin antibody is administered to achieve a serum trough concentration above 15 μg/ml for at least 20 weeks.

In certain embodiments, the polypeptide that inhibits MAdCAM-α4β7 integrin binding is administered at least once before the immune oncology treatment.

In some particular embodiments, the polypeptide that inhibits MAdCAM-α4β7 integrin binding is administered at least four times, where the second dose is administered about two weeks after the first administration, the third dose is administered about four weeks after the first administration, and the fourth dose is administered about 12 weeks after the first administration.

In certain embodiments, the polypeptide that inhibits MAdCAM-α4β7 integrin binding is administered as primary prophylaxis to a patient to be treated with immunotherapy, e.g., an immune oncology treatment, before emergence of one or more symptoms of gi-irAEs. In other embodiments, the polypeptide that inhibits MAdCAM-α4β7 integrin binding is administered in a treatment setting, in response to one or more symptoms of gi-irAEs after immune oncology treatment.

In some embodiments, the subject is undergoing treatment with (or, in certain particular embodiments, is administered) an anti-PD-1 antibody, such as an anti-PD-1 antibody that competes with nivolumab for binding PD-1, or more particularly, where the antibody has the epitopic specificity of nivolumab, or more particularly where the antibody comprises the complementarity determining regions (CDRs) of nivolumab, or still more particularly where the antibody is nivolumab. In certain embodiments, the anti-PD-1 antibody treatment is at a dose of about: 0.5-6.0 mg/kg. In particular embodiments, the dose is between about: 0.5 to 2.0 mg/kg, 0.5 to 1.5 mg/kg, 0.75 to 1.25 mg/kg, e.g., about 1.0 mg/kg. In other particular embodiments, the dose is between about: 1.5 to 6.0 mg/kg, 2.0 to 5.0 mg/kg, 2.0 to 4.0 mg/kg, 2.5 to 3.5 mg/kg, e.g., about 3.0 mg/kg. In another embodiment, the anti-PD-1 antibody treatment is a flat dose, e.g., about 200 mg, 220 mg, 240 mg, 250 mg, 260 mg, or 280 mg. The anti-PD-1 antibody can be administered at any of the foregoing doses on a variety of schedules, such as once every 1, 2, 3, 4, 5, 6, 7, 8, 9, 10, 11, or 12 weeks, or more, for, e.g., 1, 2, 3, 4, 5, 6, 7, 8, 9, 10 administrations, or more, e.g., including use without a predetermined end point. In particular embodiments, the anti-PD-1 antibody is administered at a dose of about 1 mg/kg once every two weeks or once every three weeks. In particular embodiments, the anti-PD-1 antibody is administered at a dose of about 3 mg/kg once every two weeks.

In certain embodiments, the subject is undergoing treatment with (or, in certain particular embodiments, is administered) an anti-CTLA4 antibody, such as an anti-CTLA4 antibody that competes with ipilimumab for binding CTLA4, or more particularly, an antibody that has the epitopic specificity of ipilimumab, still more particularly where the antibody comprises the complementarity determining regions (CDRs) of ipilimumab, and still more particularly where the antibody is ipilimumab. In particular embodiments, the anti-CTLA4 antibody is administered at a dose of about: 1.5 to 10.0 mg/kg (e.g., up to about 10 mg/kg), 2.0 to 5.0 mg/kg, 2.0 to 4.0 mg/kg, 2.5 to 3.5 mg/kg, or about 3.0 mg/kg. The anti-CTLA4 antibody can be administered at any of the foregoing doses on a variety of schedules, such as once every 1, 2, 3, 4, 5, 6, 7, 8, 9, 10, 11, or 12 weeks, or more, for, e.g., 1, 2, 3, 4, 5, 6, 7, 8, 9, 10 administrations, or more, e.g., use without a predetermined end point. In particular embodiments, the anti-CTLA4 antibody is administered at a dose of about 1 mg/kg once every three weeks, once every six weeks, or once every 12 weeks.

In particular embodiments, the subject being treated by the methods provided by the invention is a human, such as an adult human.

In certain embodiments, the subject being treated by the methods provided by the invention has a cancer selected from: melanoma (including unresectable or metastatic melanoma), non-small cell lung cancer (both squamous and non-squamous), renal cell carcinoma, head and neck cancer, bladder cancer, small cell lung cancer, colorectal cancer (including metastatic), prostate cancer (including metastatic hormone-refractory prostate cancer), Hodgkin lymphoma, non-Hodgkin lymphoma, and myeloma. In some embodiments, the subject being treated by the methods provided by the invention has a cancer selected from: melanoma (including unresectable or metastatic melanoma), non-small cell lung cancer (both squamous and non-squamous), renal cell carcinoma, head and neck cancer, bladder cancer, small cell lung cancer, prostate cancer (including metastatic hormone-refractory prostate cancer), Hodgkin lymphoma, non-Hodgkin lymphoma, and myeloma. In more particular embodiments, the subject has melanoma or non-small cell lung cancer. In certain particular embodiments, the subject has melanoma, including unresectable or metastatic melanoma. In other particular embodiments, the subject has non-small cell lung cancer, including both squamous and non-squamous non-small cell lung cancer.

In some embodiments, following at least one administration of the polypeptide that inhibits MAdCAM-α4β7 integrin binding, the subject is undergoing treatment with a PD-1 antagonist, such as an anti-PD-1 antibody, which is administered every two weeks, e.g., at a dose of about 3 mg/kg. In other embodiments, following at least one administration of the polypeptide that inhibits MAdCAM-α4β7 integrin binding, the subject is undergoing treatment with a CTLA4 antagonist, such as an anti-CTLA4 antibody, and is administered every three weeks, e.g., at a dose of about 3 mg/kg, concurrently with a PD-1 antagonist, e.g., at a dose of about 1 mg/kg. In still other embodiments, the subject is undergoing treatment with a CTLA4 antagonist, such as an anti-CTLA4 antibody, which is administered every three weeks, e.g., at a dose of about 3 mg/kg, concurrently with a PD-1 antagonist (such as an anti-PD-1 antibody, e.g., at a dose of about 1 mg/kg), where, following four administrations of the CTLA4 antagonist, no further CTLA4 antagonist is administered and the PD-1 antagonist, such as an anti-PD-1 antibody, is administered every two weeks (e.g., at a dose of about 3 mg/kg). In other particular embodiments, an anti-PD-1 antibody and an anti-CTLA4 antibody are both administered at a dose of about 1 mg/kg once every three weeks. In some particular embodiments, the anti-PD-1 antibody is administered at a dose of about 1 mg/kg once every two weeks and the anti-CTLA4 antibody is administered at a dose of about 1 mg/kg once every six weeks. In other particular embodiments, the anti-PD-1 antibody is administered at a dose of about 3 mg/kg once every two weeks and the anti-CTLA4 antibody is administered at a dose of about 1 mg/kg once every 12 weeks. In still other particular embodiments, the anti-PD-1 antibody is administered at a dose of about 3 mg/kg once every two weeks and the anti-CTLA4 antibody is administered at a dose of about 1 mg/kg once every six weeks. In any of the embodiments described herein, an anti-CTLA4 antibody, such as ipilimumab, can be administered at an adjuvant dose, e.g., about 10 mg/kg, e.g., every three weeks, e.g., for four doses. In any of the embodiments described herein, an anti-PD-1 antibody, an anti-CTLA4 antibody, or both an anti-PD-1 antibody and an anti-CTLA4 antibody may be administered on the same day as the polypeptide that inhibits MAdCAM-α4β7 integrin binding is administered.

In certain embodiments a subject receiving a polypeptide that inhibits MAdCAM-α4β7 integrin binding, relative to a suitable control undergoing an immune oncology treatment but not the polypeptide that inhibits MAdCAM-α4β7 integrin binding, exhibits one or more of: increased compliance (e.g., reduced incidence of treatment interruption, discontinuation, or dose reduction; higher rate of treatment completion, longer treatment duration); such as at least: 5, 10, 15, 20, 25, 30, 35, 40, 45, 50%, or more, increased compliance; no significant reduction of efficacy of the immune oncology treatment (e.g., less than 30, 25, 20, 15, 10, or 5% reduction in efficacy; or in some embodiments, increased efficacy, like 5, 10, 20, 30, 40, 50, 60, 70, 80, 90, or 100%, or more, increase in efficacy); reduced grade of gi-irAE (e.g., a reduced average grade of at least 1, 2, 3, 4 or 5 grades, or reduced frequencies of a given grade, where grades are determined by NCI CTCAE 4.03), reduced duration of gi-irAE (e.g. at least: 5, 10, 15, 20, 25, 30, 35, 40, 45, or 50% reduced duration, e.g., reduced by 1, 2, 3, 4, 5, or 6 weeks; 1, 2, 3, 4, 5, or 6 months, or longer), delayed onset of gi-irAE (delayed by 1, 2, 3, 4, 5, or 6 weeks; 1, 2, 3, 4, 5, or 6 months, or longer), reducing or eliminating the use of: corticosteroids (oral or systemic), antibiotics (oral or parenteral), non-corticosteroid immunosuppressive medication (e.g. anti-TNF-α agents), lower endoscopy, hospitalizations, or a combination thereof; (e.g. at least: 5, 10, 15, 20, 25, 30, 35, 40, 45, 50, 60, 70, 80, 90, 95, or 99% reduced); or a combination thereof.

In a related aspect, the invention also provides kits useful for performing any of the methods provided by the invention, e.g., comprising containers containing an effective amount of a polypeptide that inhibits MAdCAM-α4β7 integrin binding along with instructions for using the polypeptide to treat or prevent a gi-irAE (e.g., in a cancer subject, e.g., a subject undergoing an immune oncology treatment). In some embodiments, the kits may further comprise the components of an immune oncology treatment described herein, such as, for example, an anti-PD-1 antibody and/or an anti-CTLA4 antibody.

DETAILED DESCRIPTION

Figure 1:
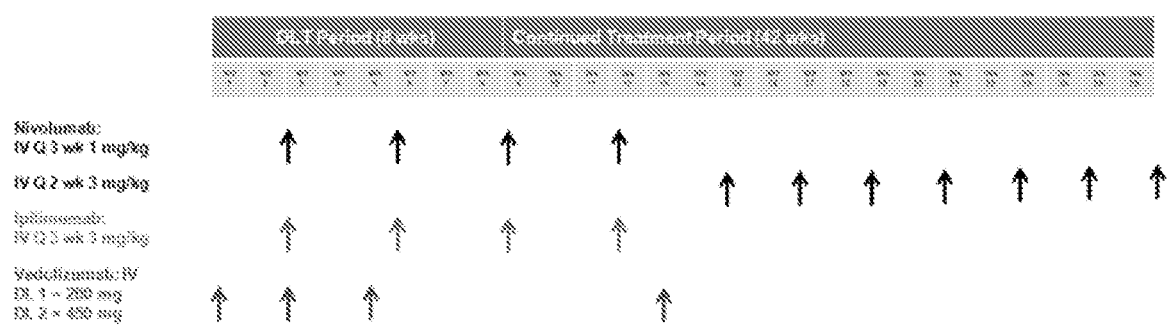
FIG. 1 is a graphic depiction of a dosing schedule of a treatment consonant with the methods provided by the invention. Depicted are administrations of an anti-α4β7 antibody (vedolizumab) together with an anti-CTLA4 antibody (ipilimumab) anti-PD-1 antibody (nivolumab) combination treatment.

The invention provides, inter alia, treatments for gastrointestinal immune-related adverse events (gi-irAE), such as colitis and diarrhea, in a mammalian subject undergoing an immune oncology treatment, such as a treatment with a PD-1 antagonist, a CTLA4 antagonist, or both a PD-1 antagonist and a CTLA4 antagonist. These treatments encompass administering a therapeutically effective amount of a polypeptide that inhibits MAdCAM-α4β7 integrin binding to the subject. "Treatment" refers to both therapeutic treatment, i.e. for those already with gi-irAE, as well as preventative treatment, when a polypeptide that inhibits MAdCAM-α4β7 integrin binding is administered to the subject before the emergence of a gi-irAE. Both therapeutic and preventative treatments can result in gi-irAE "prevention," which refers to a treatment that results in the absence or reduction in the severity of an adverse event. In a population of subjects, when treatment typically results in a certain percentage of adverse events, or a certain percentage of adverse events that are severe, but a treatment administered for prevention purposes instead results in a lower percentage of adverse events (i.e., a lower or reduced risk of adverse events) or a lower percentage of adverse events that are severe (i.e., a lower or reduced risk that the adverse event is severe) the population includes subjects for which a gi-irAE is prevented.

An "immune-related adverse event" (irAE) is an undesirable disorder induced, or exacerbated, by the on-target effect of an immune treatment, such as an immune oncology treatment. Exemplary irAEs include colitis, diarrhea, dermatitis, hepatitis, endocrinopathies, uveitis, nephritis, and combinations thereof. IrAEs can be severe, resulting in treatment delays, interruptions or discontinuations. In particular embodiments, an immune-related adverse event is a "gastrointestinal immune-related adverse event" (gi-irAE), which is an irAE of the gastrointestinal system, i.e., an undesirable acute disorder of gastrointestinal system induced, or exacerbated, by the on-target effect of an immune treatment, such as an immune oncology treatment. Thus, a gi-irAE is contrasted to a gastrointestinal disorder caused by an infectious agent (e.g., virus, bacteria, fungus, or protist), or a spontaneous and/or chronic autoimmune disease, e.g., inflammatory bowel disease, such as ulcerative colitis or Crohn's disease. Particular gi-irAEs include colitis, ileitis and diarrhea. In some embodiments, an existing infectious agent or spontaneous autoimmune disease or IBD, e.g., ulcerative colitis or Crohn's disease will be significantly exacerbated by an immune oncology treatment and, in these embodiments, are gi-irAEs. In certain particular embodiments, a gi-irAE is induced by an immune oncology treatment, such as the combination of a PD-1 antagonist and a CTLA4 antagonist.

"Immune treatment(s)" are therapeutic interventions that activate the immune system to ameliorate a condition, e.g., with one or more biologics (including antibodies, therapeutic proteins, or cells, such as modified cells, e.g., chimeric antigen receptor (CAR)-T cells), one or more small molecules, or a combination thereof. Immune treatments include agonizing immune system activators (positive regulators of the immune system), antagonizing immune system suppressors (e.g., checkpoint inhibitors), or agonizing immune system activators and antagonizing immune system suppressors. An "immune oncology treatment" is an anti-cancer immune treatment that activates the immune system, e.g., to counteract the immune-suppressive tumor microenvironment that can lead to tumors evading the immune system. Exemplary immune oncology treatments include treatment with: a PD-1 (OMIM 600244, human geneID 5133, Homologene 3681) antagonist, such as an anti-PD-1 antibody; a CTLA4 (OMIM 123890; human geneID 1493, Homologene 3820) antagonist, such as an anti-CTLA4 antibody; or both a PD-1 antagonist and a CTLA4 antagonist. Other immune oncology treatments include CCR2 antagonists (e.g., anti-CCR2 antibodies, such as plozalizumab and related antibodies), pan-RAF kinase inhibitors (i.e., a kinase inhibitor that inhibits more than just the BRAF (wt) and/or BRAFV600 isoforms, see e.g., WO 2009/006389, WO 2015/148828, WO 2010/064722; e.g., MLN2480, CAS 1096708-71-2, which can be administered at a dose of about 300 to about 600 mg, weekly), and combinations thereof, including combinations with PD-1 antagonists and/or CTLA4 antagonists. In certain embodiments, immune oncology treatments can be combined with other anti-cancer treatments, such as surgery, chemotherapy, and radiation.

A "polypeptide that inhibits MAdCAM-α4β7 integrin binding" inhibits the interaction between α4β7 integrin and MAdCAM (OMIM102670; human GeneID 8174). These polypeptides include antibodies that bind an integrin protein complex comprising an α4 integrin (OMIM 192975, human GeneID 3676, Homologene 37364), a β7 integrin (OMIM 147559; human GeneID 3695, Homologene 20247), or an α4β7 integrin complex. Administering a polypeptide that inhibits MAdCAM-α4β7 integrin binding to inhibit α4β7 integrin activity is "anti-α4β7 integrin therapy." In certain particular embodiments, a polypeptide that inhibits MAdCAM-α4β7 integrin binding is an anti-α4β7 integrin antibody, such as an antibody that will only bind α4 or β7 in the presence of the other, such as vedolizumab or a related antibody, or an antigen-binding fragment thereof. In other embodiments, the anti-α4β7 integrin antibody is AMG181 (specific for α4β7, see, e.g., U.S. Pat. No. 8,444,981), etrolizumab (β7-specific, CAS 1044758-60-2, KEGG D09901, PubChem 124490613; see, e.g., U.S. Pat. No. 7,528,236), natalizumab (α4-specific, TYSABRI®, CAS 189261-10-7, KEGG D06886, PubChem 49661786; see, e.g., U.S. Pat. No. 5,840,299), a related antibody of any of the foregoing, an antigen-binding fragment of any of the foregoing, or a combination thereof. Treatment methods using anti-α4β7 integrin antibodies are described in publication nos. U.S. 2005/0095238, WO2012151248 and WO 2012/151247.

Other polypeptides that inhibit MAdCAM-α4β7 integrin binding and can be used consonant with the invention include: anti-MAdCAM antibodies (see, e.g., U.S. Pat. No. 8,277,808, PF-00547659 or antibodies described in WO2005/067620); soluble integrin subunits (e.g., complexes comprising α4 and/or β7, which lack a transmembrane domain or lack a transmembrane and intracellular domains) such as soluble α4 integrin, soluble β7 integrin, or soluble α4β7 integrin complex, including fusion proteins, such as Fc fusions, comprising soluble integrin subunits; and soluble MAdCAM (e.g., lacking a transmembrane domain or lacking a transmembrane and intracellular domains), including fusion proteins comprising MAdCAM, such as MAdCAM-Fc chimera, as described in, for example, U.S. Pat. No. 7,803,904.

The methods provided by the invention, in certain embodiments, entail using antibodies. "Antibody" refers to an immunoglobulin or a part thereof, and encompasses any polypeptide comprising an antigen-binding site regardless of the source, species of origin, method of production, and characteristics. As a non-limiting example, the term "antibody" includes human, orangutan, mouse, rat, rabbit, goat, sheep, and chicken antibodies. The term includes but is not limited to polyclonal, monoclonal, monospecific, polyspecific, non-specific, humanized, camelized, single-chain, chimeric, synthetic, recombinant, hybrid, mutated, and CDR-grafted antibodies. For the purposes of the present invention, it also includes, unless otherwise stated, antibody fragments such as Fab, F(ab')2, Fv, scFv, Fd, dAb, VHH (also referred to as nanobodies), and other antibody fragments that retain the antigen-binding function. The term "antigen-binding domain" refers to the part of an antibody that comprises the area specifically binding to or complementary to a part or all of an antigen. Where an antigen is large, an antibody may only bind to a particular part of the antigen. The "epitope" or "antigenic determinant" is a portion of an antigen molecule that is responsible for specific interactions with the antigen-binding domain of an antibody. An antigen-binding domain may be provided by one or more antibody variable domains (e.g., a so-called Fd antibody fragment consisting of a VH domain). An antigen-binding domain can comprise an antibody light chain variable region (VL) and an antibody heavy chain variable region (VH). Antibody variable regions comprise complementary determining regions (CDRs), which together determine the specificity of the antibody. Antibodies from camels and llamas (Camelidae, camelids) include a unique kind of antibody, which is formed by heavy chains only and is devoid of light chains. The antigen-binding site of such antibodies is one single domain, referred to as VHH. Antibodies raised, or engineered, to have this topology have been termed "camelized antibodies" or "nanobodies". See, e.g., U.S. Pat. Nos. 5,800,988 and 6,005,079 and International Application Publication Nos. WO 94/04678 and WO 94/25591, which are incorporated by reference. In particular embodiments, antibodies for use in the methods provided by the invention are human, humanized, or chimeric. Antibodies for use in the methods provided by the invention can use different framework regions in different embodiments, including human: IgG1, IgG2, IgG3, or IgG4, including chimera thereof.

In some embodiments, particular antibodies discussed in the application—or related antibodies—are used in the methods provided by the invention. An antibody that is a "related antibody" (which encompasses a "related antigen-binding fragment") of a reference antibody encompasses antibodies (and antigen-binding fragments thereof) that: compete with the reference antibody for binding the target antigen (e.g., in some embodiments, competition for the same, overlapping, or adjacent epitopes), have the epitopic specificity of the reference antibody, comprise the complementarity determining regions (CDRs) of the reference antibody (in some embodiments, there may be up to 1, 2, 3, 4, or 5 conservative amino acid substitutions in the whole of the CDRs, or up to 1 or 2 conservative substitutions in each CDR), or comprise the variable heavy and variable light domains of the reference antibody (or may have at least 80, 85, 90, 95, 96, 97, 98, 99%, or more amino acid identity to the variable domains, where any amino acid changes are in the framework region and may be conservative or non-conservative). In some embodiments, conservative substitutions are determined by BLASTp's default parameters, while, in other embodiments, conservative mutations are within class substitutions, where the classes are aliphatic (glycine, alanine, valine, leucine, isoleucine), hydroxyl or sulphur/selenium-containing (serine, cysteine, selenocysteine, threonine, methionine), cyclic (proline), armotaic (phenylalanine, tyrosine, tryptophan), basic (histidine, lysine, arginine), and acidic and amides (aspartate, glutamate, asparagine, glutamine). Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity. Thus, for example, a vedolizumab related antibody, in different embodiments may, for example, compete with vedolizumab for binding α4β7 integrin, have the epitopic specificity of vedolizumab, comprise the complementarity determining regions (CDRs) of vedolizumab, or comprise the variable heavy and variable light domains of vedolizumab.

In some embodiments of the methods provided by the invention, an antibody can be replaced with an antigen-binding molecule based on a scaffold other than an immunoglobulin. For example, non-immunoglobulin scaffolds known in the art include small modular immunopharmaceuticals (see, e.g., U.S. Patent Application Publication Nos. 20080181892 and 20080227958), tetranectins, fibronectin domains (e.g., AdNectins, see U.S. Patent Application Publication No. 2007/0082365, published Apr. 12, 2007), protein A, lipocalins (see, e.g., U.S. Pat. No. 7,118,915), ankyrin repeats, and thioredoxin. Molecules based on non-immunoglobulin scaffolds are generally produced by in vitro selection of libraries by phage display (see, e.g., Hoogenboom, *Method Mol. Biol.* 178:1-37 (2002)), ribosome display (see, e.g., Hanes et al., *FEBS Lett.* 450:105-110 (1999) and He and Taussig, *J. Immunol. Methods* 297:73-82 (2005)), or other techniques known in the art (see also Binz et al., *Nat. Biotech.* 23:1257-68 (2005); Rothe et al., *FASEB J.* 20:1599-1610 (2006); and U.S. Pat. Nos. 7,270,950; 6,518,018; and 6,281,344) to identify high-affinity binding sequences.

Immune Oncology Treatments

In certain embodiments, an immune oncology treatment includes treatment with: a PD-1 antagonist, such as an anti-PD-1 antibody, such as nivolumab or pembrolizumab; a CTLA4 antagonist, such as an anti-CTLA4 antibody, such as ipilimumab or tremilimumab; or both a PD-1 antagonist and a CTLA4 antagonist. Other immune oncology treatments include CCR2 (human GeneID 729230) antagonists (e.g., anti-CCR2 antibodies), pan-RAF kinase inhibitors (e.g., MLN2480, CAS 1096708-71-2), and combinations thereof, including combinations with PD-1 antagonists and/or CTLA4 antagonists. In certain embodiments, immune oncology treatments can be combined with other anti-cancer treatments, such as surgery, chemotherapy, and radiation.

In certain embodiments, immune oncology treatments can include modulating T-cell co-receptors. In some embodiments, this encompasses agonizing one or more activating receptors or immune modulators including soluble mediators (e.g., CD28, 41BB, OX40, CD27, GITR, CD137, HVEM or a combination thereof), antagonizing one or more inhibiting receptors or immune modulators including soluble mediators (e.g., CTLA4, BTLA-4, PD-1, PDL-1, PDL-2, IDO, LAG3, ICOS, VISTA, TIM3, CSF-1R or a combination thereof), or a combination thereof, e.g., agonizing one or more activating receptors and antagonizing one or more inhibiting receptors. In some embodiments, immune oncology treatments include modulating: target classes such as: B7 and CD28-related (e.g., PDL-1, B7H3, B7H4, PD-1, CTLA4, or a combination thereof), TNF/TNFR-related (e.g., VISTA, CD40, CD40L, 4-1BB, OX40, CD27, GITR, or a combination thereof), suppressor myeloid (e.g., CSF1R), soluble mediators (e.g., IDO, CXCR4, or a combination thereof), NK cells (e.g., KIR's, NKG2A/D, CD244, or a combination thereof), Ig super family (e.g., LAG3, TIM3, or a combination thereof), and combinations of the foregoing. Thus, in certain embodiments, an immune oncology treatment includes providing one or more modulators of: 4-1BB (human GeneID 3604), B7H3 (human GeneID 80381), B7H4 (human GeneID 79679), CD27 (human GeneID 939), CD40 (human GeneID 958), CD40L (human GeneID 959), CD244 (human GeneID 51744), CSF1R (human GeneID 1436), CTLA4, CXCR4 (human GeneID 7852), GITR (human GeneID 8784), IDO (human GeneID 3620), ICOS (human GeneID 29851), KIR's (KIR2DL1 human GeneID 3802, KIR2DL3 human GeneID 3804), NKG2A (human GeneID 3821), NKG2D (human GeneID 22914), OX40 (human GeneID 7293), PD-1, PDL-1 (human GeneID 29126), PD-L2 (human GeneID 80380), TIM-3 (human GeneID 84868), VISTA (human GeneID 64115), or a combination thereof, e.g., one or more modulators for a single target or one or more modulators for two or more targets.

In some embodiments, an immune oncology treatment consonant with the present invention, e.g., for which a polypeptide that inhibits MAdCAM-α4β7 integrin binding is indicated, can include immune oncology treatments which agonize immune activation, such as an OX40 agonist, a CD27 agonist, a GITR agonist, a 4-1BB agonist, or a CD40 agonist, and those which antagonize one or more negative checkpoints, such as a PD-1 or PD-L1 antagonist, an ICOS antagonist, a LAGS antagonist, an IDO1 antagonist, or a TIM3 antagonist, or a combination of any of the foregoing, such as a GITR agonist with a PD1 antagonist. Such molecules can be large, such as antibodies or antibody-related agents, e.g., for the cell surface receptors, such as OX40 (CD134), CD27, CD40, or small, for the intracellular or enzyme targets, such as IDO1.

In certain embodiments, an immune oncology treatment consonant with the present invention, e.g., for which a polypeptide that inhibits MAdCAM-α4β7 integrin binding is indicated, is selected from: a combination of a CTLA4 antagonist (such as ipilimumab) with: a PD-1 antagonist (e.g., nivolumab), an OX40 agonist (MEDI6469 antibody, see Powderly et al., *J. Clin. Oncol.* 33, 2015 (suppl; abstr TPS3091), Eggermont and Robert, *Nat. Rev. Clin. Oncol.* 11:181-2 (2014), a CD27 agonist (e.g., varlilumab, CELL-DEX Therapeutics, see, e.g., Ramakrishna et al., *J. Immunother. Cancer* 3:27 (2015), U.S. Pat. No. 9,169,325), a KIR antagonist (e.g., lirilumab, see e.g. CAS: 1000676-41-4, KEGG: D10444, PubChem: 172232537), or an IDO antagonist (e.g., INCB024360 (epacadostat), see, e.g., PubChem 914471-09-3); a combination of a PD-1 antagonist (e.g., nivolumab) with: a CTLA4 antagonist (e.g., ipilimumab), or a 41BB agonist (e.g., PF05082566); or a combination of the foregoing.

In certain embodiments, the polypeptide that inhibits MAdCAM-α4β7 integrin binding, e.g., an antibody that comprises the CDRs of vedolizumab, is administered as primary prophylaxis to a patient to be treated with an immune oncology treatment, before emergence of one or more symptoms of gi-irAEs. In other embodiments, the polypeptide that inhibits MAdCAM-α4β7 integrin binding, e.g., an antibody that comprises the CDRs of vedolizumab, is administered in a treatment setting, in response to one or more symptoms of gi-irAEs after or during immune oncology treatment. The decision of whether to use the polypeptide that inhibits MAdCAM-α4β7 integrin binding, e.g., an antibody that comprises the CDRs of vedolizumab, for prophylaxis or treatment can result from the behavior of the immune oncology treatment alone. For example, if an immune oncology treatment causes gi-irAEs in fewer than 30% of patients, then the polypeptide that inhibits MAdCAM-α4β7 integrin binding, e.g., an antibody that comprises the CDRs of vedolizumab, is administered in a treatment setting. If an immune oncology treatment causes gi-irAEs in 30% to 50% of patients, then the polypeptide that inhibits MAdCAM-α4β7 integrin binding, e.g., an antibody that comprises the CDRs of vedolizumab, is administered in either a prophylaxis setting or a treatment setting. If an immune oncology treatment causes gi-irAEs in more than 50% of patients, then the polypeptide that inhibits MAdCAM-α4β7 integrin binding, e.g., an antibody that comprises the CDRs of vedolizumab, is administered in a prophylaxis setting.

Examples of immune oncology treatments for which the polypeptide that inhibits MAdCAM-α4β7 integrin binding, e.g., an antibody that comprises the CDRs of vedolizumab, may be administered in a prophylaxis setting, or optionally a treatment setting, are immune oncology treatments which include a CTLA4 antagonist, such as an anti-CTLA4 antibody, such as ipilimumab or tremilimumab. For example, a combination of a CTLA4 antagonist and a PD1 antagonist, e.g., in melanoma, non-small cell lung cancer or head and neck cancer; a combination of a CTLA4 antagonist, such as tremelimumab, and an OX40 agonist, such as MEDI6469 antibody, e.g., in solid tumor cancer, such as metastatic colorectal cancer; a combination of a CTLA4 antagonist and a KIR antagonist, such as lirilumab, e.g., in solid tumor cancer or lymphoma; a combination of a CTLA4 antagonist, such as ipilimumab, and a CD27 agonist, such as varlilumab, e.g., in melanoma; a combination of a CTLA4 antagonist, such as ipilimumab and an IDO antagonist, such as INCB024360 (epacadostat), e.g., in melanoma; or a combination of a CTLA4 antagonist, such as tremelimumab, and an epidermal growth factor receptor (EGFR) antagonist, such as erlotinib or gefitinib, e.g., in EGFR mutated non-small cell lung cancer; may use the polypeptide that inhibits MAdCAM-α4β7 integrin binding, e.g., an antibody that comprises the CDRs of vedolizumab, is administered in a prophylaxis setting, or optionally a treatment setting.

Examples of immune oncology treatments for which the polypeptide that inhibits MAdCAM-α4β7 integrin binding, e.g., an antibody that comprises the CDRs of vedolizumab, is administered in a treatment setting, are immune oncology treatments which include a PD-1 antagonist, such as an anti-PD-1 antibody, such as nivolumab or pembrolizumab. For example, a combination of a PD-1 antagonist, such as nivolumab, and a KIR antagonist, such as lirilumab, e.g., in solid tumor cancer, such as head and neck cancer (e.g., HNSCC); a combination of a PD-1 antagonist, such as nivolumab, and a CD27 agonist, such as varlilumab, e.g., in solid tumor cancer such as head and neck cancer, ovarian carcinoma, colorectal cancer, renal cell carcinoma or glioblastoma; or a combination of a PD-1 antagonist, such as pembrolizumab, and a 4-1BB agonist, such as PF-05082566 (utomilumab), e.g., in solid tumor cancer, such as renal cell carcinoma and small cell lung cancer; may use the polypeptide that inhibits MAdCAM-α4β7 integrin binding, e.g., an antibody that comprises the CDRs of vedolizumab, is administered in a treatment setting. Additional examples of immune oncology treatments for which the polypeptide that inhibits MAdCAM-α4β7 integrin binding, e.g., an antibody that comprises the CDRs of vedolizumab, is administered in a treatment setting, are immune oncology treatments which include agents, e.g., single agents, which target TIM3, 4-1BB, B7H3, B7H4, CCR2, CD27, CD40, CD40L, CD244, CSF1R, CXCR4, GITR, IDO, ICOS, KIRs (e.g., KIR2DL1 or KIR2DL3), NKG2A, NKG2D, OX40, RAF kinase, or VISTA. For example, a combination of a PD-1 antagonist, such as nivolumab, and GITR activator, e.g., may be used in treatment of ovarian cancer.

PD-1 Antagonists

Programmed Death 1 protein (PD-1) is recognized as an important player in immune regulation and the maintenance of peripheral tolerance. PD-1 is moderately expressed on naive T, B and NKT cells and up-regulated by T/B cell receptor signaling on lymphocytes, monocytes and myeloid cells (Sharpe, A. H, et al. (2007) Nature Immunology; 8:239-245).

"PD-1 antagonist" means any chemical compound or biological molecule that regulates (in particular embodiments, block or inhibit) the interaction with PD-1 and its cognate ligands (e.g. PD-L1 and/or PD-L2) expressed on the surface of interacting cell types such as T cells, cancer cells, macrophages and antigen presenting cells (APCs). Alternative names or synonyms for PD-1 (human GeneID 29126) and its ligands include: PDCD1, PD1, CD279 and SLEB2 for PD-1; PDCD1L1, PD-L1, B7H1, B7-4, CD274 and B7-H for PD-L1; and PDCD1L2, PDL2, B7-DC, Btdc and CD273 for PD-L2. In any of the treatment methods, medicaments and uses of the present invention in which a human subject is being treated, the PD-1 antagonist inhibits or blocks binding of human PD-L1 to human PD-1, and preferably inhibits or blocks binding of both human PD-L1 and PD-L2 to human PD-1. Human PD-1 amino acid sequences can be found in NCBI Locus No.: NP 005009. Human PD-L1 and PD-L2 amino acid sequences can be found in NCBI Locus No.: NP_054862 and NP_079515, respectively.

PD-1 antagonists useful in any of the treatment methods, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in some embodiments, the human constant region is an IgG1 or IgG4 constant region. In some embodiments, the antigen binding fragment is selected from the group consisting of Fab, Fab'-SH, F(ab')2, scFv and Fv fragments. Administering a PD-1 antagonist to inhibit PD-1 activity is an "anti-PD-1 treatment."

Examples of mAbs that bind to human PD-1, and are useful in the treatment methods, medicaments and uses of the present invention, are described in U.S. Pat. Nos. 7,521,051, 8,779,105, 8,008,449, 8,900,587, 8,952,136, 8,354,509, 8,735,553, 9,102,728, 8,993,731, 9,102,727, 9,181,342, 8,927,697, 8,945,561, U.S. Pat. No. 748,802, U.S. Pat. Nos. 7,322,582, 7,524,498 and 9,205,148. Specific anti-human PD-1 mAbs useful as the PD-1 antagonist in the treatment methods, medicaments and uses of the present invention include, but are not limited to: pembrolizumab (formerly MK-3475 and lambrolizumab; see CAS: 1374853-91-4, KEGG: D10574), marketed in the USA under the tradename KEYTRUDA®, a humanized IgG4 mAb with the structure described in WHO Drug Information, Vol. 27, No. 2, pages 161-162 (2013) or a related antibody; nivolumab (formerly ONO-4538, MDX1106 or BMS-936558; see CAS: 946414-94-4, KEGG: D10316, PubChem: 163312346), marketed in the USA under the tradename OPDIVO®, a human IgG4 mAb with the structure described in WHO Drug Information, Vol. 27, No. 1, pages 68-69 (2013), or a related antibody; pidilizumab (also known as CT-011, hBAT or hBAT-1; see CAS: 1036730-42-3, PubChem: 172232483, KEGG: D10390) a human IgG1 mAb with the structure described in WHO Drug Information, Vol. 26, No. 4, page 434 (2012), or a related antibody; and the humanized antibodies h409A11, h409A16 and h409A17, which are described in WO2008/156712, or related antibodies; PDR-100; SHR-1210; REGN-2810; MEDI-0680; BGB-108; and PF-06801591.

Examples of mAbs that bind to human PD-L1, and useful in the treatment methods, medicaments and uses of the present invention, are described in WO2013/019906, WO2010/077634, and U.S. Pat. No. 8,383,796. Specific anti-human PD-L1 mAbs useful as the PD-1 antagonist in the treatment methods, medicaments and uses of the present invention include, but are not limited to atezolizumab (MPDL3280A), BMS-936559, durvalumab (MEDI4736), avelumab (MSB0010718C) and an antibody which comprises the heavy chain and light chain variable regions of SEQ ID NO:24 and SEQ ID NO:21, respectively, of WO2013/019906, or comprise the CDRs of these variable domains.

Other PD-1 antagonists useful in the any of the treatment methods, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010/027827 and WO2011/066342. Specific fusion proteins useful as the PD-1 antagonist in the treatment methods, medicaments and uses of the present invention include AMP-224 (also known as B7-DCIg), which is a PD-L2-FC fusion protein and binds to human PD-1.

In some embodiments, the PD-1 antagonist is selected from nivolumab, pembrolizumab, PDR-001, SHR-1210, AMP-224, REGN-2810, MEDI-0680, BGB-108, PF-06801591, atezolizumab, durvalumab, and BMS-936559, and AMP-224.

In some embodiments, the PD-1 antagonist is selected from nivolumab, pembrolizumab, PDR-001, SHR-1210, AMP-224, REGN-2810, MEDI-0680, BGB-108, and PF-06801591, and AMP-224.

In some embodiments, the PD-1 antagonist is selected from pembrolizumab and nivolumab.

In some embodiments, the PD-1 antagonist is nivolumab.

In some embodiments, the PD-1 antagonist is pembrolizumab.

In some embodiments, the PD-1 antagonist is selected from atezolizumab, durvalumab, and BMS-936559.

In some embodiments of the treatment methods, medicaments and uses of the present invention, the PD-1 antagonist is a monoclonal antibody, or antigen binding fragment thereof, which comprises an antigen binding fragment of nivolumab.

In some embodiments of the treatment methods, medicaments and uses of the present invention, the PD-1 antagonist is a monoclonal antibody, or antigen binding fragment thereof, which comprises an antigen binding fragment of pembrolizumab.

In other embodiments of the treatment methods, medicaments and uses of the present invention, the PD-1 antagonist is a monoclonal antibody, or antigen binding fragment thereof, which specifically binds to human PD-1 and comprises (a) a heavy chain variable region of an antibody described herein or a variant thereof, and (b) a light chain variable region of an antibody described herein or a variant thereof. In some embodiments, a variant of a heavy chain variable region sequence is identical to the reference sequence except having up to seventeen conservative amino acid substitutions in the framework region (i.e., outside of the CDRs), and preferably has less than ten, nine, eight, seven, six or five conservative amino acid substitutions in the framework region. In certain embodiments, a variant of a light chain variable region sequence is identical to the reference sequence except having up to five conservative amino acid substitutions in the framework region (i.e., outside of the CDRs), and preferably has less than four, three, or two conservative amino acid substitutions in the framework region.

CTLA4 Antagonists

Human CTLA4 (CYTOTOXIC T LYMPHOCYTE-ASSOCIATED 4, a.k.a. CD152) is an immunoglobulin superfamily protein expressed on activated T cells. Human versions of the CTLA4 gene were cloned in the late 1980's and early 1990's. Sequences and homologs for CTLA4 are known and readily available. See, for example, OMIM 123890; human geneID 1493, Homologene 3820 for reference sequences, which are incorporated by reference. Soluble CTLA4 acts, at least in part, to block CD28-mediated T-cell activation, thus inhibiting CTLA4 can, inter alia, de-repress T-cell activation and activate the immune system, which, in turn, can then attack cancer cells. One way to inhibit CTLA4 is with anti-CTLA4 antibodies or antigen binding fragments thereof. Use of CTLA4 antagonists for inhibiting CTLA4 activity is an "anti-CTLA4 therapy." CTLA4 antagonists include anti-CTLA4 antibodies.

In particular embodiments, an anti-CTLA4 antibody for use in the methods provided by the invention is ipilimumab (sold under the trade name YERVOY®, registered by Bristol-Myers Squibb Company) or a related antibody or antigen-binding fragment thereof. U.S. Pat. Nos. 6,984,720 and 7,605,238 provide sequences for ipilimumab, and are incorporated by reference. See also CAS 477202-00-9, PubChem 47206447, and Kegg D04603.

Other antibodies for anti-CTLA4 treatment in the methods provided by the invention include those described in: U.S. Pat. Nos. 6,682,736 and 8,883,984 (Pfizer, Amgen; describing tremelimumab/ticilimumab) and related antibodies; U.S. Pat. No. 7,034,121 (Genetics Institute) and related antibodies; US20030086930A1 and related antibodies; Patent Application Publication No WO2006029219A2 and related antibodies; U.S. Pat. No. 8,263,073 and related antibodies, which increase T cell response without inhibiting CTLA4 binding to B7 ligands; U.S. Pat. No. 8,697,845 and related antibodies, which are specific to the soluble form of CTLA4; US20140105914, which are humanized, and related antibodies; WO2016015675 and related antibodies. The foregoing publications are incorporated by reference for their description of anti-CTLA4 antibodies useful in the methods provided by the invention, as well as combinations of the antibodies with each other and combination regimens described in the publications.

U.S. Pat. No. 9,084,776, which is incorporated by reference, describes combination methods using anti-PD-1 antibodies in conjunction with CTLA4 antibodies for cancer treatment that can be adapted for use consonant with the present invention, i.e., by administering one or more polypeptides that inhibit MAdCAM-α4β7 integrin binding to ameliorate gi-irAEs from the anti-PD-1 therapy/anti-CTLA4 therapy combination. The combination methods using anti-CTLA4 antibodies with chemotherapeutic agents described in U.S. Pat. No. 8,685,394 may also be adapted for use in the present invention, e.g., by administering one or more polypeptides that inhibit MAdCAM-α4β7 integrin binding to ameliorate gi-irAEs from the anti-CTLA4 treatment combination, which may, optionally, also be included with, for example, an anti-PD-1 treatment. Also, the methods that combine anti-CTLA4 antibodies with light-activated therapy described in U.S. Pat. No. 8,226,946 can be adapted for use in the methods provided by the invention analogously, e.g., a light-activated therapy can be combined with anti-CTLA4 treatment and/or anti-PD-1 treatment, and one or more polypeptides that inhibit MAdCAM-α4β7 integrin binding are provided to ameliorate gi-irAEs. U.S. Patent Application Publication No. 20100330093 describes combinations of various CTLA4 antibodies with thymosin peptides and these antibodies, and related antibodies, can be used alone, or in combination with thymosin peptides consonant with the invention. The combination anti-CTLA4 antibodies with anti-CD137 (agonist) therapy in described in U.S. Pat. No. 8,475,790 can also be enhanced by the methods provided by the invention, e.g., by administering one or more polypeptides that inhibit MAdCAM-α4β7 integrin binding to ameliorate gi-irAEs from the combination. Additional anti-CTLA4 treatment combination therapies that may benefit from the methods provided by the invention, e.g., by administering one or more polypeptides that inhibit MAdCAM-α4β7 integrin binding to ameliorate gi-irAEs, are described in: US20130156768A1 (describing combination treatments with anti-CTLA4 treatment and BRAF inhibitors), WO2013019620A2 (describing combinations treatments with anti-CTLA4 treatment, BRAF inhibitors, and MEK inhibitors), US20150283234A1 (anti-CTLA4 treatment and anti-KIR treatment combinations), US20140323533A1 (anti-CTLA4 in combination with tubulin modulators), WO2015058048A1 (which describes combinations with VEGF antagonists), US20150328311 (describing combinations with MEDI4736), WO2015125159A1 (describing combinations with IL-2RP agonists, optionally with anti-PD-1 treatment).

The anti-CTLA4 treatment dosing schedules described in U.S. Pat. No. 9,062,111 can be used in the methods provided by the invention and are incorporated by reference, as are the methods described in U.S. Patent Application Publication No. 20150079100A1, which reduce clearance of anti-CTLA4 antibodies from a subject.

Polypeptides that Inhibit MADCAM-α4β7 Integrin Binding

The cell surface molecule, "α4β7 integrin," or "α4β7," is a heterodimer of an $α_4$ chain (CD49D, ITGA4) and a $β_7$ chain (ITGB7). Each chain can form a heterodimer with an alternative integrin chain, to form $α_4β_1$ or $α_Eβ_7$. Human $α_4$ and $α_7$ genes (GenBank (National Center for Biotechnology Information, Bethesda, Md.) RefSeq Accession numbers NM_000885 and NM_000889, respectively) are expressed by B and T lymphocytes, particularly memory CD4+ lymphocytes. Typical of many integrins, α4β7 can exist in either a resting or activated state. Ligands for α4β7 integrin include vascular cell adhesion molecule (VCAM), fibronectin, and mucosal addressin (MAdCAM (e.g., MAdCAM-1)). The α4β7 integrin mediates lymphocyte trafficking to GI mucosa and gut-associated lymphoid tissue (GALT) through adhesive interaction with mucosal addressin cell adhesion molecule-1 (MAdCAM-1), which is expressed on the endothelium of mesenteric lymph nodes and GI mucosa.

As noted supra, a variety of polypeptides can inhibit MAdCAM-α4β7 integrin binding, including: anti-α4β7 antibodies, anti-MAdCAM antibodies, soluble integrin subunits (including fusion proteins, such as Fc-fusions), and soluble MAdCAM (including fusion proteins, such as Fc-fusions). Use of any of these polypeptides to inhibit MAdCAM-α4β7 integrin binding is an "anti-α4β7 treatment."

Anti-α4β7 Integrin Antibodies

Anti-α4β7 antibodies for use in the methods provided by the invention can, in certain embodiments, bind to an epitope on the α4 chain (e.g., humanized MAb 21.6 (Bendig et al., U.S. Pat. No. 5,840,299), on the β7 chain (e.g., FIB504 or a humanized derivative (e.g., Fong et al., U.S. Pat. No. 7,528,236)), or to a combinatorial epitope formed by the association of the α4 chain with the β7 chain. In one aspect, the antibody is specific for the α4β7 integrin complex, e.g., the antibody binds a combinatorial epitope on the α4β7 complex, but does not bind an epitope on the α4 chain or the β7 chain unless the chains are in association with each other. The association of α4 integrin with β7 integrin can create a combinatorial epitope for example, by bringing into proximity residues present on both chains which together comprise the epitope or by conformationally exposing on one chain, e.g., the α4 integrin chain or the β7 integrin chain, an epitopic binding site that is inaccessible to antibody binding in the absence of the proper integrin partner or in the absence of integrin activation. In another aspect, the anti-α4β7 antibody binds both the α4 integrin chain and the β7 integrin chain, and thus, is specific for the α4β7 integrin complex. Such antibodies, which are specific for the α4β7 integrin complex, can bind α4β7 but not bind α4β1, and/or not bind $α_Eβ7$, for example. In another aspect, the anti-α4β7 antibody binds to the same or substantially the same epitope as the Act-1 antibody (Lazarovits, A. I. et al., *J. Immunol.*, 133(4): 1857-1862 (1984), Schweighoffer et al., *J. Immunol.*, 151(2): 717-729, 1993; Bednarczyk et al., *J. Biol. Chem.*, 269(11): 8348-8354, 1994). Murine ACT-1 Hybridoma cell line, which produces the murine Act-1 monoclonal antibody, was deposited under the provisions of the Budapest Treaty on Aug. 22, 2001, on behalf of Millennium Pharmaceuticals, Inc., 40 Landsowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-α4β7 antibody is a human antibody or an α4β7 binding protein using the CDRs provided in U.S. Patent Application Publication No. 2010/0254975.

In one aspect, the anti-α4β7 antibody inhibits binding of α4β7 to one or more of its ligands (e.g. the mucosal addressin, e.g., MAdCAM (e.g., MAdCAM-1), fibronectin, and/or vascular addressin (VCAM)). Primate MAdCAMs are described in the PCT publication WO 96/24673, the entire teachings of which are incorporated herein by this reference. In another aspect, the anti-α4β7 antibody inhibits binding of α4β7 to MAdCAM (e.g., MAdCAM-1) and/or fibronectin without inhibiting the binding of VCAM.

Vedolizumab and Related Antibodies

In certain embodiments, an anti-α4β7 antibody for use in the methods provided by the invention is vedolizumab (CAS Registry number 943609-66-3, American Chemical Society) or a related antibody. In some particular embodiments, the anti-α4β7 antibodies are humanized versions of the mouse Act-1 antibody discussed supra. Generally, the humanized anti-α4β7 antibody will contain a heavy chain that contains the three heavy chain complementarity determining regions (CDRs, CDR1, SEQ ID NO:4, CDR2, SEQ ID NO:5 and CDR3, SEQ ID NO:6) of the mouse Act-1 antibody and suitable human heavy chain framework regions; and also contain a light chain that contains the three light chain CDRs (CDR1, SEQ ID NO: 7, CDR2, SEQ ID NO: 8 and CDR3, SEQ ID NO: 9) of the mouse Act-1 antibody and suitable human light chain framework regions. The humanized Act-1 antibody can contain any suitable human framework regions, including consensus framework regions, with or without amino acid substitutions. For example, one or more of the framework amino acids can be replaced with another amino acid, such as the amino acid at the corresponding position in the mouse Act-1 antibody. The human constant region or portion thereof, if present, can be derived from the κ or λ light chains, and/or the γ (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference.

In other particular embodiments, the anti-α4β7 humanized antibodies for use in the methods provided by the invention comprise a heavy chain variable region of vedolizumab, e.g., comprising amino acids 20 to 140 of SEQ ID NO:1 and a light chain variable region of vedolizumab or a variant sequence, e.g., comprising amino acids 20 to 131 of SEQ ID NO:2 or amino acids 1 to 112 of SEQ ID NO:3. If desired, a suitable human constant region(s) can be present. For example, the humanized anti-α4β7 antibody can comprise a heavy chain that comprises amino acids 20 to 470 of SEQ ID NO:1 and a light chain comprising amino acids 1 to 219 of SEQ ID NO:3. In another example, the humanized anti-α4β7 antibody can comprise a heavy chain that comprises amino acids 20 to 470 of SEQ ID NO:1 and a light chain comprising amino acids 20 to 238 of SEQ ID NO:2. The humanized light chain of vedolizumab with two mouse residues switched for human residues, is more human than the light chain of LDP-02 (compare SEQ ID NO: 2 to 3). In addition, LDP-02 has the somewhat hydrophobic, flexible alanine 114 and a hydrophilic site (Aspartate 115) that are replaced in vedolizumab with the slightly hydrophilic hydroxyl-containing threonine and hydrophobic, potentially inward facing valine residue, respectively.

Further substitutions to the antibody sequence can be, for example, mutations to the heavy and light chain framework regions, such as a mutation of isoleucine to valine on residue 2 of human GM607 CL kappa light chain variable region; a mutation of methionine to valine on residue 4 of human GM607 CL kappa light chain variable region; a mutation of alanine to glycine on residue 24 of human 21/28 CL heavy chain variable region; a mutation of arginine to lysine at residue 38 of 21/28 CL heavy chain variable region; a mutation of alanine to arginine at residue 40 of 21/28 CL heavy chain variable region; a mutation of methionine to isoleucine on residue 48 of 21/28 CL heavy chain variable region; a mutation of isoleucine to leucine on residue 69 of 21/28 CL heavy chain variable region; a mutation of arginine to valine on residue 71 of 21/28 CL heavy chain variable region; a mutation of threonine to isoleucine on residue 73 of 21/28 CL heavy chain variable region; or any combination thereof; and replacement of the heavy chain CDRs with the CDRs (CDR1, SEQ ID NO:4, CDR2, SEQ ID NO:5 and CDR3, SEQ ID NO:6) of the mouse Act-1 antibody; and replacement of the light chain CDRs with the light chain CDRs (CDR1, SEQ ID NO:7, CDR2, SEQ ID NO:8 and CDR3, SEQ ID NO:9) of the mouse Act-1 antibody.

In some embodiments, the anti-α4β7 humanized antibodies for use in the methods provided by the invention comprise a heavy chain variable region that has at least about: 95%, 96%, 97%, 98%, or 99% sequence identity to amino acids 20 to 140 of SEQ ID NO:1 (e.g., are 100% identical), and a light chain variable region that has at least about: 95%, 96%, 97%, 98%, or 99% sequence identity to amino acids 20 to 131 of SEQ ID NO:2 or amino acids 1 to 112 of SEQ ID NO:3 (e.g. are 100% identical to either of these reference sequences). In some embodiments, anti-α4β7 humanized antibodies may have 1, 2, 3, 4, 5, 6, 7, 8, 9, 10, or more, amino acid substitutions relative to the foregoing reference sequences. In some embodiments, any amino acid substitutions are conservative substitutions. In other embodiments, amino acid substitutions are non-conservative. In certain embodiments, amino acid substitutions are in the framework regions. In other embodiments, substitutions can be in the CDRs and in these embodiments, the substitutions are preferably conservative Amino acid sequence identity can be determined using a suitable sequence alignment algorithm, such as the Lasergene system (DNASTAR, Inc., Madison, Wis.) or BLASTp using the default parameters. In certain particular embodiments, the anti-α4β7 antibody for use in the methods provided by the invention is vedolizumab (CAS, American Chemical Society, Registry number 943609-66-3).

Vedolizumab and related antibodies may be administered in the methods provided by the invention by any suitable method, such as by one or more of intravenous injection, subcutaneous injection, or infusion. Formulations suitable for intravenous injection, which may be prepared in lyophilized form, are described in U.S. Patent Application Publication No. 20140377251, which is incorporated by reference. Stable liquid formulations suitable for, e.g., subcutaneous injection are described in U.S. Patent Application Publication No. 20140341885, which is incorporated by reference.

In some embodiments, vedolizumab is administered at a dose of 50 mg, 100 mg, 108 mg, 165 mg, 200 mg, 216 mg, 300 mg, 450 mg, 500 mg, or more. In some embodiments, the vedolizumab is administered, for example subcutaneously, at a dose of 0.05 mg/kg, 0.10 mg/kg, 0.15 mg/kg, 0.2 mg/kg, 0.25 mg/kg, 0.3 mg/kg, 0.4 mg/kg, or 0.5 mg/kg, at a dose of 108 mg, 200 mg, 216 mg, 450 mg, 160 mg or 165 mg. The vedolizumab may be administered once per day, per week, per month, or per year. In some embodiments, the vedolizumab is administered at zero, two and six weeks, and then every four weeks or every eight weeks thereafter. In some embodiments, vedolizumab is administered one or more times, and then at least one month, at least six months, or at least one year later, vedolizumab is again administered one or more times. In some embodiments, 200, 300, or 450 mg vedolizumab may be administered by intravenous infusion at zero, two, and six weeks, and then at four weeks intervals or eight week intervals thereafter. In some embodiments, 200, 300, or 450 mg vedolizumab may be administered by intravenous infusion at zero, two, and six weeks, and then at two, three or four week intervals, 108, 165, or 216 mg of vedolizumab may be administered subcutaneously. In some embodiments, 200, 450, or 600 mg vedolizumab may be administered by intravenous infusion at zero, two, and four weeks, and then a final dose is administered at about 75, 80, 85, 90, 95, or 100 days, e.g., between about 85 to about 90 days, between about 75 to about 90 days or between about 85 to about 100 days.

Treatment and Prevention of gi-irAEs

The invention provides, inter alia, methods of treating gi-irAEs (or treating cancer, e.g., by treating gi-irAEs) in a subject by inhibiting MAdCAM-α4β7 integrin binding. In certain embodiments, a subject treated according to the methods provided by the invention, relative to a suitable control undergoing an immune oncology treatment (e.g., with a PD-1 antagonist, a CTLA4 antagonist, or both a PD-1 antagonist and a CTLA4 antagonist), but not the polypeptide that inhibits MAdCAM-α4β7 integrin binding, the subject exhibits one or more of: increased compliance (e.g., reduced incidence of treatment interruption, dose reduction, or discontinuation, higher rate of treatment completion, longer treatment duration), such as at least: 5, 10, 15, 20, 25, 30, 35, 40, 45, 50%, or more, increased compliance; no significant reduction of efficacy of the immune oncology treatment (e.g., less than 30, 25, 20, 15, 10, or 5% reduction in efficacy; or in some embodiments, increased efficacy, like 5, 10, 20, 30, 40, 50, 60, 70, 80, 90, or 100%, or more, increase in efficacy); reduced grade of gi-irAE (e.g., a reduction of the average grade of at least 1, 2, 3, 4 or 5 grades; or reductions in frequency of 20, 30, 40, 50, 60, 70, 80, 90, or 100%, or more of subjects with a particular grade of a gi-irAE, such as colitis or diarrhea), reduced duration of gi-irAE (e.g. at least: 5, 10, 15, 20, 25, 30, 35, 40, 45, or 50% reduced duration, e.g., reduced by 1, 2, 3, 4, 5, or 6 weeks; 1, 2, 3, 4, 5, or 6 months, or longer), delayed onset of gi-irAE (delayed by 1, 2, 3, 4, 5, or 6 weeks; 1, 2, 3, 4, 5, or 6 months, or longer), reducing or eliminating the use of: corticosteroids (oral or systemic), antibiotics (oral or parenteral), non-corticosteroid immunosuppressive medication, lower endoscopy, hospitalizations, or a combination thereof (e.g. at least: 5, 10, 15, 20, 25, 30, 35, 40, 45, 50, 60, 70, 80, 90, 95, or 99% reduced); or a combination of any of the foregoing.

In a recent metanalysis with 2774 patients receiving checkpoint inhibitors (CTLA-4 and/or PD-1), diarrhea frequency was 11% to 51% and colitis 1% to 16%. The relative risk (RR) of all-grade diarrhea was 1.64 (95% CI: 1.19-2.26; p=0.002). For colitis, it was 10.35 (95% CI: 5.78-18.53; p<0.00001). In another metanalysis (N=1571) assessing ipilimumab-associated diarrhea, the overall incidence of all-grade diarrhea was 41.6% (95% CI: 33.6%-50.0%). In this analysis, the overall incidence of Grade≥3 diarrhea was 8.4% (95% CI: 5.5%-12.7%). Ipilimumab RR for all-grade diarrhea is 1.63 (95% CI: 1.37-1.97; p<0.001) and for Grade≥3 diarrhea is 2.19 (95% CI: 1.11-4.34; p=0.025). The median time for the occurrence of Grade 2/3 colitis with ipilimumab is 6.5 weeks. In a recent phase 3 trial in patients with melanoma who were treated with the combination of nivolumab plus ipilimumab, the incidence of diarrhea was 44% with 9% Grade 3/4. Colitis was diagnosed in 12% of patients with 8% Grade 3/4. Enterocolitis is more frequently associated with CTLA-4 inhibition than with PD-1 inhibitors. The methods provided by the invention can ameliorate these complications in whole or in part.

Irrespective of grade, nearly half of patients with irAEs receiving ipililumab (monotherapy or in combination) required treatment interruption and immune modulatory medication (systemic corticosteroids with/out infliximab). Half of these irAEs leading to treatment interruption/discontinuation are diarrhea/colitis. Current guidelines for the management of colitis/diarrhea indicates treatment interruption if it is ≥Grade 2 and starting prednisone if continues at Grade 2 longer than 5 days or immediately if Grade 3 or greater. Treatment can only be re-started after symptom improvement and steroids tapering over 1 month. All this creates major difficulties in treatment compliance. Currently systemic steroids at 1-2 mg/kg followed by infliximab if symptoms are not remitting are used empirically without clinical trial supportive evidence. Only budesonide—a corticosteroid indicated to treat inflammatory bowel disease (IBD)—has been evaluated in a randomized clinical trial to prevent ipilimumab-induced colitis—with negative results. Again, the methods provided by the invention can ameliorate these complications in whole or in part, without many of the complications of existing interventions.

An inhibitor of MAdCAM-α4β7 integrin binding restricts its activity to the GI tract and gut lymph tissue and its use in the prevention of gi-irAEs will 1) have no negative impact on T-cell trafficking to tumor or T-cell subpopulations within the tumor microenvironment, and 2) reduce treatment-associated gi-irAEs resulting in clinical benefit with a better safety profile in patients with cancer, such as advanced melanoma, receiving checkpoint inhibitor combination therapy. For example, in some embodiments, subjects treated by the methods provided by the invention exhibit reduced, or in some embodiments, no grade 3 or 4 (no: Grade 3 colitis, Grade 4 (or Grade 3 that persists or worsens over 3-5 days) colitis or diarrhea), only grade 1-2 diarrhea, or if any grade 2 occurs, that the symptoms resolve, e.g., by symptomatic antidiarrheal treatment without adding prednisone or anti-TNF-α treatment; or reduced, or in some embodiments, no grade 1 or 2 symptoms. In other embodiments, no, or reduced, grade 4 diarrhea is observed; more particularly, where no, or reduced, grade 3 diarrhea is observed; still more particularly, no, or reduced, grade 2 diarrhea is observed, or still more particularly, no, or reduced, grade 1 diarrhea is observed. In still other embodiments, no, or reduced, grade 4 colitis is observed; more particularly, no, or reduced, grade 3 colitis is observed; still more particularly, no, or reduced, grade 2 colitis is observed, or still more particularly, no, or reduced, grade 1 colitis is observed. In yet other embodiments, no, or reduced, grade 4 colitis or diarrhea is observed; more particularly, where no, or reduced, grade 3 colitis or diarrhea is observed; still more particularly, no, or reduced, grade 2 colitis or diarrhea is observed, or still more particularly, no, or reduced, grade 1 colitis or diarrhea is observed. In other embodiments, the methods provided by the invention reduce, or eliminate the frequency of grade 2 symptoms that persist >5 days or recur, for which 0.5 to 2 mg/kg/day prednisone equivalents is normally indicated (with a 1 month tapering of steroids once grade 1 or lower is achieved) with suggested prophylactic antibiotics for opportunistic infections; i.e., the methods provided by the invention reduce or eliminate the need for corticosteroids and/or prophylactic antibiotics. In still further embodiments, the methods provided by the invention reduce or eliminate the frequency of grade 3 symptoms requiring intervention, such as treatment discontinuation, and administration of corticosteroids at a dose of 1 to 2 mg/kg/day prednisone equivalents, and/or prophylactic antibiotics for opportunistic infections and/or lower endoscopy, and/or hospitalization; i.e., the methods provided by the invention reduce or eliminate the need for corticosteroids, and/or prophylactic antibiotics, and/or lower endoscopy, and/or hospitalization. In yet other embodiments, the methods provided by the invention reduce, or eliminate the frequency of grade 4 symptoms requiring intervention, such as treatment discontinuation, and administration of corticosteroids at a dose of 1 to 2 mg/kg/day prednisone equivalents, and/or prophylactic antibiotics for opportunistic infections, and/or lower endoscopy and/or non-corticosteroid immunosuppressive medication, and/or hospitalization; i.e., the methods provided by the invention reduce or eliminate the need for corticosteroids, and/or prophylactic antibiotics, and/or lower endoscopy, and/or non-corticosteroid immunosuppressive medication, and/or hospitalization. In certain embodiments, the methods provided by the invention delay the onset of gi-irAEs, e.g., the occurrence, of colitis and/or diarrhea is delayed beyond the typical 5-10 week peak occurrence (peak~week 8), e.g., the methods provided by the invention delay the onset of gi-irAEs by 2, 4, 5, 6, 8, 10 weeks or more; and more particularly, delay the onset and reduce the frequency and/or severity of gi-irAEs that do occur, e.g., by 1, 2, 3, 4, 5, or 6 weeks; 1, 2, 3, 4, 5, or 6 months, or longer.

In some embodiments of the present invention, the following gradings apply: Grade 1 (Diarrhea <4 stools per day over baseline; colitis: asymptomatic; clinical or diagnostic observations only); Grade 2 (diarrhea: 4-6 stools/day over base line; IV fluids indicated <24 hours; not interfering with activities of daily living [ADL]; colitis: abdominal pain, blood in stool); Grade 3 (diarrhea: ≥7 stools/day over baseline; IV fluids ≥24 hours; interfering with activities of daily living (ADL); colitis: severe abdominal pain, medical intervention indicated, peritoneal signs); Grade 4 (colitis: life-threatening, perforation). In certain embodiments grades of gi-irAEs, such as colitis or diarrhea are determined by NCI CTCAE 4.03.

EXEMPLIFICATION

Example 1

A phase 1b study to evaluate the safety, tolerability, and pharmacodynamics of an investigational treatment of vedolizumab in combination with standard of care immune checkpoint inhibitors in patients with advanced melanoma is undertaken. Up to about 52 subjects are enrolled. Approximately 12 subjects are assigned in dose-escalation treatments, with up to 46 subjects in an expansion. From 2-15 sites support the subjects.

The subjects are adults, either male or female, with histologically confirmed, unresectable stage III or IV melanoma, according to the AJCC staging system, and with a ECOG performance status of 0-1. Subjects have adequate bone marrow reserve and renal and hepatic function. Subjects with active known or suspected autoimmune disease, or that are undergoing systemic treatment with either corticosteroids (>10 mg prednisone or equivalents) or other immunosuppressive medications within 14 days of administration of a study drug administration, are excluded, as are subjects with prior treatment with an anti-PD-1, anti-PDL-1, anti-PDL-2, or anti-CTLA4 antibodies.

Vedolizumab is administered by IV at a dose of 200 or 450 mg at weeks 1, 3, 5, and 13. Nivolumab is administered IV at a dose of 3 mg/kg Q2W, which is the standard of care. Standard of care for nivolumab together with ipilimumab is administered as follows. Nivolumab (1 mg/kg) and ipilimumab (3 mg/kg) are both administered IV, Q3W for 4 doses, after which nivolumab (3 mg/kg) is administered IV Q2W until disease progression or unacceptable toxicity. Duration of treatment is up to 50 weeks and the period of evaluation is 12 months. FIG. 1 provides a graphic description of this dosing schedule.

The primary endpoint for this study is the frequency and severity of treatment-emergent adverse events (TEAEs, e.g., colitis or diarrhea), including serious TEAEs. Secondary endpoints for this study are measures of disease response including objective response rate (ORR) as assessed by the investigator, duration of response (DOR), and progression-free survival (PFS) based on the investigator's assessment using the RECIST guidelines v1.1 and overall survival (OS). Serial tumor biopsies are also collected and quantification of changes in infiltrating immune cells and other putative biomarkers using methods including but not limited to immunohistochemistry and gene-expression profiling, post-single agent and post-combination treatment are completed.

Example 2

An amended phase 1b study to evaluate the safety, tolerability, and pharmacodynamics of an investigational treatment of vedolizumab in combination with standard of care immune checkpoint inhibitors in patients with advanced melanoma is undertaken. Up to about 52 subjects are enrolled. Approximately 12 subjects are assigned in dose-escalation treatments, with up to 46 subjects in an expansion. From 2-15 sites support the subjects.

The subjects are adults, either male or female, with histologically confirmed, unresectable stage III or IV melanoma, according to the AJCC staging system, and with a ECOG performance status of 0-1. Subjects have adequate bone marrow reserve and renal and hepatic function. Subjects with active known or suspected autoimmune disease, or that are undergoing systemic treatment with either corticosteroids (>10 mg prednisone or equivalents) or other immunosuppressive medications within 14 days of administration of a study drug administration, are excluded, as are subjects with prior treatment with an anti-PD-1, anti-PDL-1, anti-PDL-2, or anti-CTLA4 antibodies.

Figure 2:
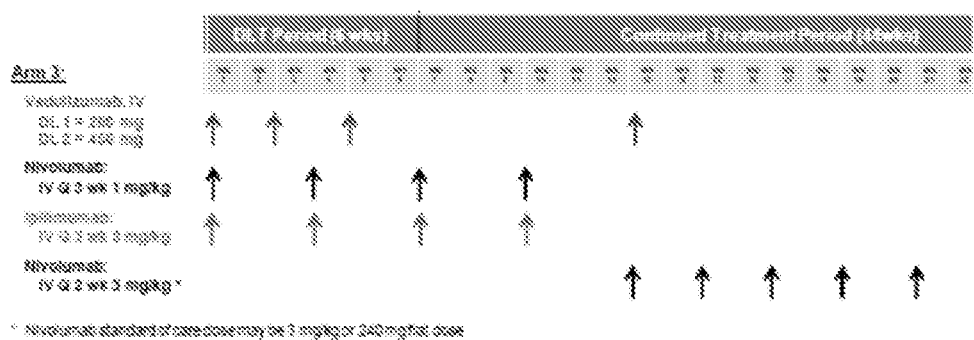
FIG. 2 is a graphic depiction of an alternative dosing schedule of a treatment consonant with the methods provided by the invention. Depicted are administration of an anti-α4β7 antibody (vedolizumab) together with an anti-CTLA4 antibody (ipilimumab) anti-PD-1 antibody (nivolumab) combination treatment.

Vedolizumab is administered by IV at a dose of 200 or 450 mg at weeks 1, 3, 5, and 13. Nivolumab (1 mg/kg) and ipilimumab (1 mg/kg) are both administered IV, Q3W for 4 doses, after which nivolumab (3 mg/kg or 240 kg flat dose) is administered IV beginning on week 13, day 85 Q2W until disease progression or unacceptable toxicity. Duration of treatment is up to 50 weeks and the period of evaluation is 12 months. FIG. 2 provides a graphic description of this dosing schedule.

The primary endpoint for this study is the frequency and severity of treatment-emergent adverse events (TEAEs, e.g., colitis or diarrhea), including serious TEAEs. Secondary endpoints for this study are measures of disease response including objective response rate (ORR) as assessed by the investigator, duration of response (DOR), and progression-free survival (PFS) based on the investigator's assessment using the RECIST guidelines v1.1 and overall survival. Changes of microbiome composition and fecal calprotectin in stool samples posttreatment are compared to pretreatment, and changes in serum levels of C-reactive protein pre- and posttreatment are measured.

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or other accession numbers (typically referencing National Center for Biotechnology Information (NCBI) accession numbers), including, for example, genomic loci, genomic sequences, functional annotations, allelic variants, and reference mRNA (including, e.g., exon boundaries or response elements) and protein sequences (such as conserved domain structures), Homologene, OMIM, as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The foregoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

---

INFORMAL SEQUENCE LISTING

>SEQ ID NO: 1
>heavy chain of humanized anti-α4β7 Ig;
italicized sequence is leader sequence;
underlined sequences are CDRs
*MGWSCIILFLVATATGVHS*QVQLVQSGAEVKKPGASVKVSCKGSGYTFT<u>S
YWMH</u>WVRQAPGQRLEWIG<u>EIDPSESNTNYNQKFKG</u>RVTLTVDISASTAYM
ELSSLRSEDTAVYYCAR<u>GGYDGWDYAIDY</u>WGQGTLVTVSSASTKGPSVFP
LAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCP
PCPAPELAGAPSVFLFPPKPKDTLMISRTPEVTCVVVDVSHEDPEVKFNW
YVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDI
AVEWESNGQPENNYKTTPPVLDSGSFFLYSKLTVDKSRWQQGNVFSCSV
MHEALHNHYTQKSLSLSPGK*

>SEQ ID NO: 2
>light chain of humanized anti-α4β7 Ig;
italicized sequence is leader sequence;
underlined sequences are CDRs; bold,
underline, italicized sequence is end of
variable region

*MGWSCIILFLVATATGVHS*DVVMTQSPLSLPVTPGEPASISC<u>RSSQSLAK
SYGNTYLS</u>WYLQKPGQSPQLLIY<u>GISNRFS</u>GVPDRFSGSGSGTDFTLKIS
RVEAEDVGVYYC<u>LQGTHQPYT</u>FGQGTKVEI*K*RTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC*

>SEQ ID NO: 3
>Mature humanized light chain of LDP-02;
underlined sequences are CDRs; bold, underline,
italicized sequence is end of variable region DVVMTQSPLSLPVTPGEPASISC<u>RSSQSLAKSYGNTYLS</u>WYLQKPGQSPQ
LLIY<u>GISNRFS</u>GVPDRFSGSGSGTDFTLKISRVEAEDVGVYYC<u>LQGTHQP
YT</u>FGQGTKVEI*K*RADAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC*

| SEQ ID NO: 4 | SYWMH | CDR1 of heavy chain mouse ACT-1 antibody |
|---|---|---|
| SEQ ID NO: 5 | EIDPSESNTNYNQKFKG | CDR2 of heavy chain mouse ACT-1 antibody |
| SEQ ID NO: 6 | GGYDGWDYAIDY | CDR3 of heavy chain mouse ACT-1 antibody |
| SEQ ID NO: 7 | RSSQSLAKSYGNTYLS | CDR1 of light chain mouse ACT-1 antibody |
| SEQ ID NO: 8 | GISNRFS | CDR2 of light chain mouse ACT-1 antibody |
| SEQ ID NO: 9 | LQGTHQPYT | CDR3 of light chain mouse ACT-1 antibody |

---

The invention claimed is:

1. A method of treating a gastrointestinal immune-related adverse event (gi-irAE) in a human subject having advanced melanoma and undergoing an immune oncology treatment comprising treatment with ipilimumab and nivolumab, said method comprising administering four doses of a therapeutically effective amount of an anti-α4β7 integrin antibody to the human subject who has advanced melanoma, and is undergoing concurrent immune oncology treatment comprising treatment with ipilimumab and nivolumab, such that the gi-irAE is treated,
   wherein the antibody is administered in response to symptoms of a gi-riAE which is Grade 3 or 4 diarrhea,
   wherein the antibody comprises the complementarity determining regions (CDRs):
   Light chain:
      CDR1 SEQ ID NO:7
      CDR2 SEQ ID NO:8 and
      CDR3 SEQ ID NO:9; and
   Heavy chain:
      CDR1 SEQ ID NO:4
      CDR2 SEQ ID NO:5 and
      CDR3 SEQ ID NO:6, and
   wherein the subject exhibits no significant reduction of efficacy of the immune oncology treatment after administration of the anti-α4β7 integrin antibody.

2. The method of claim 1, wherein the anti-α4β7 integrin antibody comprises the heavy chain variable region of SEQ ID NO:1 and the light chain variable region of SEQ ID NO:2 or SEQ ID NO:3.

3. The method of claim 1, wherein the anti-α4β7 integrin antibody is administered at a dose selected from the group consisting of 1.25 to 8.0 mg/kg, 1.25 to 4.25 mg/kg, 1.75 to 3.75 mg/kg, 2.25 to 3.25 mg/kg, 2.86 mg/kg, 5.0 to 8.0 mg/kg, 5.5 to 7.5 mg/kg, 6.0 to 7.0 mg/kg, and 6.43 mg/kg.

4. The method of claim 1, wherein the anti-α4β7 integrin antibody is administered to achieve a serum concentration of about: 10 μg/ml, or more.

5. The method of claim 1, wherein the anti-α4β7 integrin antibody is administered at a unit dose of about: 108, 150, 165, 200, 216, 250, 300, 350, 400, 450, 500, 550, 600, 650, 700, 750 mg, or more.

6. The method of claim 1, wherein, following at least one administration of the anti-α4β7 integrin antibody
    ipilimumab is administered every three weeks concurrently with nivolumab.

7. The method of claim 1, wherein, relative to a suitable control undergoing an immune oncology treatment, but does not receive the anti-α4β7 integrin antibody, the subject exhibits one or more of: increased efficacy of the immune oncology treatment, reduced grade of gi-irAE, reduced duration of gi-irAE, or a combination thereof.

8. The method of claim 1, wherein the anti-α4β7 integrin antibody is vedolizumab.

9. The method of claim 4, wherein the serum concentration is about 11 μg/ml, 12 μg/ml, 13 μg/ml, 14 μg/ml, 15 μg/ml, 16 μg/ml, 17 μg/ml, 18 μg/ml, 19 μg/ml, 20 μg/ml, 25 μg/ml, 30 μg/ml, 35 μg/ml, 40 μg/ml, 45 μg/ml, 50 μg/ml, or more.

10. The method of claim 1, wherein the melanoma is unresectable melanoma or metastatic melanoma.

11. The method of claim 1, wherein the anti-α4β7 integrin antibody is administered by intravenous infusion at a dose of 200 mg or 450 mg at zero, two, four weeks and twelve weeks or thirteen weeks.

12. The method of claim 1, wherein the anti-α4β7 integrin antibody is administered at least four times.

* * * * *

SEQUENCE LISTING

<160> NUMBER OF SEQ ID NOS: 9

<210> SEQ ID NO 1
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 1

```
Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
            20                  25                  30

Pro Gly Ala Ser Val Lys Val Ser Cys Lys Gly Ser Gly Tyr Thr Phe
        35                  40                  45

Thr Ser Tyr Trp Met His Trp Val Arg Gln Ala Pro Gly Gln Arg Leu
    50                  55                  60

Glu Trp Ile Gly Glu Ile Asp Pro Ser Glu Ser Asn Thr Asn Tyr Asn
65                  70                  75                  80

Gln Lys Phe Lys Gly Arg Val Thr Leu Thr Val Asp Ile Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Tyr Asp Gly Trp Asp Tyr Ala Ile Asp
        115                 120                 125

Tyr Trp Gly Gln Gly Thr Leu Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Ala Gly Ala Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400
```

```
Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 2
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Ala Lys Ser Tyr Gly Asn Thr Tyr Leu Ser Trp Tyr Leu Gln Lys Pro
    50                  55                  60

Gly Gln Ser Pro Gln Leu Leu Ile Tyr Gly Ile Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Leu Gln Gly Thr His Gln Pro Tyr Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 3
<211> LENGTH: 219
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 3

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Tyr Thr Phe Gly Gln Gly Thr Lys Val Glu Ile Lys
            100                 105                 110

Arg Ala Asp Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 4

```
Ser Tyr Trp Met His
1               5
```

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 5

```
Glu Ile Asp Pro Ser Glu Ser Asn Thr Asn Tyr Asn Gln Lys Phe Lys
1               5                   10                  15

Gly
```

```
<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Tyr Asp Gly Trp Asp Tyr Ala Ile Asp Tyr
1               5                   10

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ser Ser Gln Ser Leu Ala Lys Ser Tyr Gly Asn Thr Tyr Leu Ser
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Ile Ser Asn Arg Phe Ser
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Leu Gln Gly Thr His Gln Pro Tyr Thr
1               5
```